(12) United States Patent
Harichian et al.

(10) Patent No.: US 7,307,187 B1
(45) Date of Patent: Dec. 11, 2007

(54) PROCESS FOR CONVERTING PRIMARY AMIDOALCOHOLS TO AMIDOCARBOXYLIC ACIDS IN HIGH YIELD

(75) Inventors: Bijan Harichian, Brookfield, CT (US); Vivek Subramanian, Southbury, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 11/475,825

(22) Filed: Jun. 27, 2006

(51) Int. Cl.
*C07C 409/24* (2006.01)
*C07C 229/00* (2006.01)
(52) U.S. Cl. .......................... 562/6; 562/450
(58) Field of Classification Search ............. 562/6, 562/450
See application file for complete search history.

(56) References Cited

U.S. PATENT DOCUMENTS 5,175,360 A * 12/1992 Fried ..................... 562/538

FOREIGN PATENT DOCUMENTS

JP 10087554 A * 4/1998

OTHER PUBLICATIONS

Japanese Patent Laid-Open No. 05/194,334 to Sandoz (Derwent Abstract and English language translation enclosed).
Japanese Patent Laid-Open No. 04/283,537 to Shell (Derwent Abstract and Japanese patent enclosed).
Japanese Patent Laid-Open No. 10/087,554 to Lion Corp. (English language translation enclosed).
Co-pending application: Applicant: Bijan Harichian, For: Process For Converting Primary Amidoalcohols to Amidocarboxylic Acids in High Yield, Date Deposited: Jun. 27, 2006, UNUS No. 06-0188-TR, Assignee: Conopco, Inc., d/b/a UNILEVER.

* cited by examiner

*Primary Examiner*—Yvonne Eyler
*Assistant Examiner*—Lalitha Nagubandi
(74) *Attorney, Agent, or Firm*—Ronald A. Koatz

(57) ABSTRACT

The invention relates to an improved process for oxidizing a primary amidoalcohol to the corresponding amidocarboxylic acid in high yield.

12 Claims, 1 Drawing Sheet

HPLC Chromatogram of N-Lauroylglycine from Example 2

HPLC Chromatogram of N-Lauroylglycine from the Comparative Example

N-Lauroylglycine elutes at 13.5 min. Peaks coming before 5 min. are from the mobile phase, not the sample, and one therefore not integrated.

PROCESS FOR CONVERTING PRIMARY AMIDOALCOHOLS TO AMIDOCARBOXYLIC ACIDS IN HIGH YIELD

FIELD OF THE INVENTION

The present invention relates to a process for converting a compound or polymer comprising a primary alcohol and an amide group to amidocarboxylic acid. In particular, the primary amido alcohol is converted to carboxylic acid in unexpectedly high yields when proper solvent is selected.

BACKGROUND

Amidocarboxylic acids are desirable surfactants in that they have good water solubility, good detergency and foaming properties and are mild to skin and hair. One method for the production of such surfactant is through the oxidation of an alcohol containing an amide group (e.g., coco mono-ethanolamide or CMEA).

The problem, however, is that it is very difficult to drive the oxidation of alcohol to carboxylic acid efficiently. The reaction will often stop at the aldehyde stage, and the yields of carboxylic acid as final products are quite low.

Japanese Patent laid-Open No. 05/194,334 (Sandoz) discloses a process in which a hydroxyl containing compound (which may be, for example, alkyl amide polyoxyalkanol) is made to react with at least an equimolar amount of inorganic or organic halogen-containing oxidizing agent, e.g. NaOCl, in the presence of weak base and a catalytic amount of hindered nitroxide as exemplified by 2, 2, 6, 6-tetramethylpiperidine 1-oxyl, hereafter abbreviated TEMPO, and chemical derivatives thereof. In this patent, no yield or purity information is given. The process disclosed is limited to alcohols which have polyethylene glycol or polypropylene glycol substitution, or to polyglucosides, as starting reactants. Such compounds are water-soluble or water-dispersible, which makes possible the use of water as the solvent. The patent does not teach a process using hydrophobic primary alcohols (i.e., amido alcohols) of the invention as starting reactant.

Japanese Patent Laid Open No. 04/283,537 (Shell) discloses a process using an oxidizing agent such as sodium hypochlorite in the presence of TEMPO. The process relates to production of an alkoxyalkanoic acid from the corresponding alkoxyalkanol, however, and not to the production of an amidecarboxylic acid from an alcohol having an amide group.

Japanese Laid Open No. 10/087,554 (Lion Corporation) discloses a process for production of amidocarboxylic acid from alcohol having an amide group using an oxidizing agent of chlorine type (e.g. NaOCl) in the presence of a nitroxide radical (e.g., TEMPO) and further in the presence of alkali metal halide or alkali earth metal halide (e.g., potassium chloride). In Examples 3 and 5, for example, an alcohol comprising amide; a nitroxide radical; and a 10% solution of alkali metal chloride (potassium or sodium bromide) in water, additional water, and acetonitrile (solvent) are charged into a beaker and stirred. Under these conditions, the acetonitrile and water mix together to form a single liquid phase. In each example, the purity of the carboxylic acid is calculated from the acid value, but nothing is stated about yield. The acid value is not selective for the desired carboxylic acid, but would include all acid components present.

Unexpectedly, applicants have now found that the type of solvent or solvents used during the oxidation reaction is critical to the yield of product (carboxylic acid). Without wishing to be bound by theory, applicants believe the starting amidoalcohol must not be in the same phase as the oxidizing agent. Applicants have found that this separation of oxidizing agent and alcohol can be accomplished in at least two different ways. According to claims of the subject application, the final product (e.g., amidocarboxylic acid) is partitioned into an organic solvent (i.e., using solvent that will form both a hydrophobic liquid phase and an aqueous liquid phase, rather than forming one substantially aqueous phase). In this manner, the exposed amide group on the amidoalcohol is protected from cleavage (e.g., the bleach which has partitioned mainly into aqueous phase will not attack the amidoalcohol in the separate phase), and consequently far greater yield of amidocarboxylic acid is produced. That is, it is important that, in the presence of the oxidizing agent, both a solvent rich layer (substantially free of oxidizing agent) and an aqueous layer (comprising substantially of the oxidizing agent) form.

In a second embodiment, subject of applicant's copending application, the oxidizing agent and the alcohol are also maintained in separate phases. Here, however, the two phases are a water phase and a solid phase, and water alone is used as the solvent. That is, the amidoalcohol, which is hydrophobic, does not dissolve or disperse into the aqueous phase (rather it stays in the solid, non-aqueous phase) while the NaOCl remains in the continuous aqueous phase.

As indicated, the subject application relates to processes where a liquid organic solvent is employed and solvent(s) partition into at least two liquid phases. In such circumstances, applicants have further discovered that the type of solvent is a critical parameter.

BRIEF DESCRIPTION OF THE INVENTION

The present invention provides a process for converting primary alcohol having an amide group to amidocarboxylic acid in high yield (e.g., $\geq 75$, preferably $\geq 80\%$, more preferably $\geq 85\%$, more preferably $\geq 90\%$ yield) which process comprises reacting a primary alcohol having amide group (amidoalcohol) with an oxidizing agent, preferably a chlorine-containing oxidant like NaOCl, in the presence of a nitroxide radical and optionally in the presence of an alkali metal halide or alkali earth metal halide. In this process the solvent in which the reaction takes place is selected such that, in the presence of the oxidizing agent, the primary amidoalcohol partitions (after addition of bleach or other oxidizing agent) into the liquid organic phase while bleach or oxidizing agent stays substantially in liquid aqueous phase. Such partitioning ensues the high yields noted above (e.g. because the amide linkage is not available to be cleaved by the oxidizing agent which has partitioned into liquid aqueous phase). In other words, the amidoalcohol partitions quickly enough into the organic phase to avoid formation of undesired by-product. It is completely unexpected that the specific type of solvent chosen could make such critical difference.

It is also a critical aspect of the invention that the catalyst used in this reaction be a hindered nitroxide radical. An optional alkali metal halide or alkali earth metal halide co-catalyst may also to be used, or the co-catalyst can be, for example, sodium tetraborate.

Specifically, in one embodiment of the invention, sufficient base (e.g., sodium hydroxide) is added to the reaction to ensure reaction takes place at a pH above 6, preferably 7 to 10, more preferably 7.5 to 9, even more preferably 8 to 9. Addition of base is used to make up for consumption of oxidizing agent (e.g., sodium hypochlorite) during formation of amidocarboxylic acid. Base may be added to the oxidizing agent solution prior to addition of the oxidizing agent to the reaction or it may be added during the course of the reaction (e.g., to maintain constant pH).

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

Figure 1:
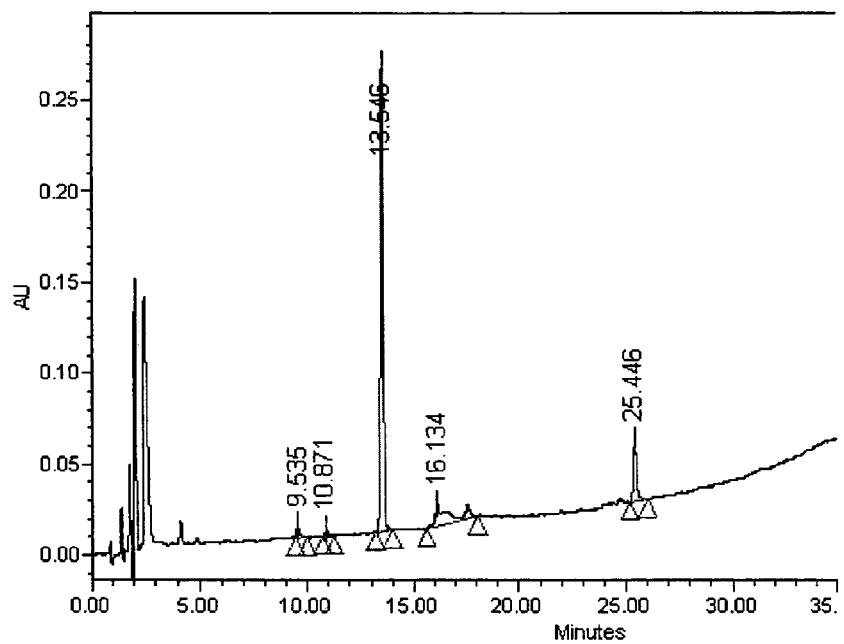
FIG. 1 is a liquid chromatogram (HPLC) profile of products formed when reaction was carried out in CH$_3$CN/water solvent and only a single liquid phase was formed (bottom FIGURE, corresponding to example of JP 10/087,554 reference to Lion), compared to when solvent was THF/water and formed two liquid phases (top).
Figure 1:
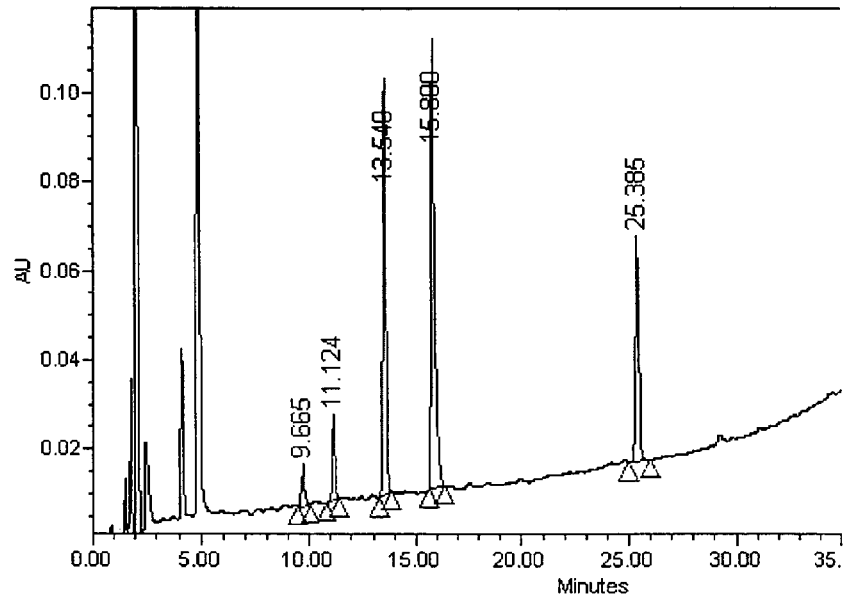

As observed, a solvent which partitions into two liquid phases leads to high yields of N-lauroylglycine (LG) from N-lauroylmonoethanolamide (LMEA) starting material. By contrast, when the organic solvent formed a single liquid phase with the water, the yield and purity of LG (glycinide) were lower. Thus, for example, the pure LG product was predominantly formed at 13.54 minutes when two liquid phases formed but, when only one phase formed, there were huge amounts of impurities at 15.80 seconds.

DETAILED DESCRIPTION OF THE INVENTION

The present invention relates to a novel and improved process for converting a primary alcohol comprising an amide group (e.g., $C_8$-$C_{22}$ alkoylmonoalkanolamide such as lauroyl monoethanolamide) to the corresponding amidocarboxylic acid (e.g., mixture of N-lauroyl glycine and alkali-metal N-lauroyl glycinate), and which process provides very high yields of product (e.g., ≧75%, preferably ≧80%, more preferably ≧85% yield). More specifically the process comprises reacting a primary alcohol comprising such amide group with an oxidizing agent in the presence of a nitroxide radical and optional catalyst (e.g., alkali metal halide), wherein the solvent in which the reaction takes place is selected in such way that two liquid phases separating the amidoalcohol from the oxidizing agent are formed. In other words, the amidoalcohol is partitioned into the liquid organic phase of the two phase system thereby and the oxidizing agent stays predominantly in the liquid aqueous phase. This protects the amide group on the amidoalcohol from further cleavage and provides the high yields as noted. In a second embodiment of the invention (claimed in copending application), the amidoalcohol is separated from the oxidizing agent using only water as solvent in that the oxidizing agent partitions into the liquid aqueous phase while the amidoalcohol stays in the undissolved solid state (heterogeneous solid-liquid system).

More specifically, the starting reactant of the subject invention is an alcohol having an amide group which may be defined as follows:

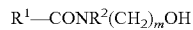

$R^1$—$CONR^2(CH_2)_m OH$ wherein $R^1$ is linear or branched alkyl or alkenyl group having 7 to 22 carbon atoms; $R^2$ is H, an alkyl or hydroxyalkyl group with 1 to 6 carbon atom(s); and m is an integer from 1 to 6.

Examples of compounds which may be encompassed by the structure are N-alkanoylmonoethanolamines such as N-lauroylmonoethanolamide (LMEA) or N-cocoylmonoethanolamide (CMEA).

The starting product may be a mixture of monoalkanolamides (e.g., monoethanolamine) including those derived from mixtures of fatty acids found in nature. N-cocoyl monoethanolamine, for example may comprise a mixture of $C_8$, $C_{10}$ and $C_{12}$ fatty acids as major component mixed with $C_{14}$, $C_{16}$ and $C_{18}$ fatty acids.

The oxidizing agent used to oxidize the starting alcohol can be any oxidizing agent which will allow the alcohol group to be oxidized to carboxylic acid. Typically, such oxidizing agents include those of the chlorine type. These may include chlorine, a hypochlorite (e.g., alkali metal hypochlorite), trichloroisocyanuric acid and dichloroisocyononic acid. Preferred oxidizing agents include sodium hypochlorite (e.g., industrial grade bleach comprises 5% to 13% sodium hypochlorite), calcium hypochlorite, chlorine itself, and organic chlorine-containing compounds, for example trichloroisocyanuric acid. Non-chlorine containing oxidants may be used, for example, oxone (2KHSO$_5$.KHSO$_4$.K$_2$SO$_4$), NaOBr, N-bromosuccinimide, or tribromoisocyanuric acid. Non-halogen containing antioxidants may also be used, as exemplified by H$_2$O$_2$, optionally in the presence of sodium tungstate dihydrate catalyst.

The amount of oxidizing agent may vary, but typically equimolar to 8 molar, preferably 1 to 7 equivalents, more preferably 2 to 6 molar are used.

The starting alcohol of the invention is oxidized with an oxidizing agent (as noted above) in the presence of a hindered piperidinyloxy radical catalyst (nitroxide) and optionally in the presence of co-catalyst as are described below.

The nitroxide catalyst radical used in the invention (e.g., hindered nitroxide) is produced by oxidation of a cyclic or acyclic secondary amine containing no α-hydrogens (i.e., there are no hydrogens on the carbon adjacent to N) with peroxide, or by oxidation of the corresponding hydroxylamine. Examples of stable nitroxide radicals suitable for use in this invention are mentioned in the following documents. These include linear, cyclic, dicyclic or macromolecular compounds to which one or more nitroxyl radicals are connected.

Chem. Review, 78, 37 (1979):

G. Rozantsev, "Free Nitroxyl Radicals", Penum Publishing Corporation, New York, 1970; and E. G. Rozantsev, V. D., Scholle, Synthesis, 1971,190.

Preferred examples of the nitroxide radical are as follows.

2,2,6,6-Tetramethyl-piperidine 1-oxyl (TEMPO);

2,2,5,5-Tetramethyl-pyrrolidine 1-oxyl; and

1-Aza-2,2,7,7-tetramethyl-cycloheptane 1-oxyl.

TEMPO and chemical derivatives thereof are preferred, examples of which follow:

4-Hydroxyl-2,2,6,6-tetramethyl-piperidine 1-oxyl;
4-Methoxy-2,2,6,6-tetramethyl-piperidine 1-oxyl;
4-Ethoxy-2-2,6,6-tetramethyl-piperidine 1-oxyl;
4-Acetylamido-2-2,6,6-tetramethyl-piperidine 1-oxyl;
4-Carbamoyl-2,2,6,6-tetramethyl-piperidine 1-oxyl;
4-Benzoylamino-2,2,6,6-tetramethyl-piperidine 1-oxyl;
4-Oxo-2,2,6,6-tetramethyl-piperidine 1-oxyl;
2,2,6,6-Tetramethyl-piperidine-1-oxyl 4-sulfate;
2,2,6,6-Tetramethyl-piperidine-1-oxyl 4-phosphate; and
3-Carbamoyl-2,2,6,6-tetramethyl-pyrrolidine 1-oxyl.

UV light stabilizers containing 2,2,6,6-tetramethylpiperidine functionality (Hindered Amine Light Stabilizers, abbreviated HALS), both monomeric and oligomeric, can serve as precursors to stable nitroxyl radicals by oxidation as well.

It is also possible that an amine or a hydroxylamine which is a precursor thereof is used and, in the actual case, it is oxidized and then used. The amount of the nitroxide radical used to 1 equivalent of the starting alcohol material is typically from 0.01 to 10 mol % or, preferably, from 0.1 to 5 mol % based on amidoalcohol.

An optional co-catalyst is often used with the nitroxide radical primary catalyst. The co-catalyst, if used, may be for example an alkali metal halide or alkali earth metal halide. These may include alkali metal bromide, e.g. sodium bromide, and alkali metal chloride, e.g. sodium chloride, and potassium chloride, alkali earth metal bromide, e.g calcium bromide and magnesium bromide, alkali earth metal chloride, e.g. calcium chloride, and magnesium chloride.

Typically the co-catalyst is used from 0.01 to 10 mole %, preferably 0.1 to 5 mol % equivalent based on amidoalcohol. Sodium tetraborate may be used in place of the bromide or chloride.

Solvent

The key to the invention resides in the selection of proper solvent, i.e., solvent which will partition into liquid organic phase and liquid aqueous phase upon combination of oxidizing agent and amidoalcohol in the solvent.

Although the ideal solvents are at least partially water miscible (e.g., tetrahydrofuran), the key is that, in the presence of oxidizing agent (e.g., aqueous sodium hypochlorite), at least two immiscible liquid layers (e.g., a solvent-rich layer, normally the upper layer; and a water-rich layer, normally the lower layer) will form.

Without wishing to be bound by theory, applicants believe it is important that the amidoalcohol not be in the same phase as the oxidizing agent when combined. Applicants have found that this can be accomplished in two different ways. According to claims of the subject invention, this can be done by partitioning the final product (amidocarboxylic acid) into a liquid organic solvent (i.e., using solvent that will form two phases, rather than forming one substantially aqueous phase). The exposed amide group on the alcohol comprising amide is thus protected from cleavage (e.g., through attack by the bleach which has partitioned mainly into separate liquid aqueous phase), and consequently far greater yield of carboxylic is produced. That is, it is important that, in the presence of the oxidizing agent, both a solvent rich layer (substantially free of oxidizing agent) and an aqueous layer (comprising substantially of the oxidizing agent) form. It should be noted that how quickly the two phase separation occurs is dependent generally on the scale of the reaction. Typically, the phase separation will occur in an hour or less, and can occur relatively instantaneously.

A second way to maintain the oxidizing agent and the alcohol in separate phases, in this case in a liquid water phase and in a solid phase, is to use water alone as the solvent. The amidoalcohol is hydrophobic and does not dissolve or disperse into the aqueous phase (it stays in solid phase), while the NaOCl remains in the continuous liquid aqueous phase.

A reaction in which the solvent will form only one liquid phase (e.g., $CH_3CN$/water solvent used in JP 10/087,554), thus, is not suitable and will form product in lower yield and purity.

Surprisingly, solvents at opposite extremes of the polarity scale may be suitable for the reaction. Suitable polar solvents may include oxygenated hydrocarbons, more specifically cyclic and acyclic ethers and polyethers. Suitable non-polar solvents may include cyclic and acyclic aliphatic solvents, and aromatic solvents.

Specific examples of cyclic oxygenated solvents (e.g. polar solvents) which may be used include tetrahydrofuren (THF) and dioxolane. Examples of acyclic oxygenated solvents include 1,2-dimethoxyethane, dimethoxymethane, diethoxymethane, and 2-methoxyethyl ether.

It is preferred that the solvents do not contain anti-oxidants (e.g., butylated hydroxyl toluene, abbreviated as BHT) as these anti-oxidants can interfere with the oxidation reaction. Such anti-oxidants are often found in cyclic and acyclic ethers and polyethers. Thus, preferably, solvents of the invention are substantially anti-oxidant free.

Specific examples of cyclic aliphatic solvents (e.g., non-polar solvents) include cyclohexane; examples of acyclic aliphatic solvents include heptanes and hexanes; and examples of aromatic solvents include toluene, o, m, or p-xylene, and mixed xylenes.

In preferred reaction, because of the consumption of oxidizing agent (e.g., sodium hypochlorite) and formation of carboxylic acid as consequence of the reaction, sufficient base should be used in the reaction to maintain pH above 6, more preferred above 7, preferably 8-9. An example of base which may be used is alkali metal hydroxide (e.g., NaOH).

The base may be added to the oxidizing agent before the oxidizing agent is added to the reaction or, alternatively, the base may be added, for example, drop-wise during the course of the reaction as needed to maintain constant pH.

The reaction itself typically takes place at room temperature, but is exothermic. Temperature rises of up to about 35° C. occur without cooling. A cooling bath can be used to reduce the exotherm.

A typical example of an oxidation of a monoethanolamide (N-lauroylmonoethanolamide, or LMEA) to N-lauroylglycine (LG), as well as reaction conditions, isolation methodology and rate of conversion to LG are set forth below:

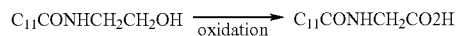
$C_{11}CONHCH_2CH_2OH \xrightarrow{\text{oxidation}} C_{11}CONHCH_2CO_2H$

| Reaction Conditions: | |
|---|---|
| Solvent: | Tetrahydrofuran (THF)/Water |
| Oxidizing agent: | NaOCl (bleach, 11.5%, 3 eq.) + NaOH (base to maintain pH) |
| Catalyst: | KBr (co-catalyst), 4-Acetamido-TEMPO (abbreviated AA-TEMPO) |
| Reaction temp: | 25-30° C. |
| pH range: | 12 (initial) to 6 (final) |
| Reaction time: | 1-4 hr. |
| Isolation: | THF extraction followed by solvent evaporation |
| Typical conversion rate: | 95-99% |

It should be noted that a mixture of N-lauroylglycine and sodium N-laurylglycinate (e.g., salt form) can be obtained depending on isolation pH and therefore, yields can be calculated separately for each.

EXAMPLES

Protocol

Extraction Technique to Isolate Carboxylic Acid (e.g., N-laurylglycine)

At completion of oxidation reaction, reaction mixture is acidified to pH about 3.0 (e.g., by addition of HCl) and layers are separated. Lower aqueous layer is extracted with THF and the combined THF layers are concentrated on a rotary evaporator and dried in vacuo to give carboxylic acid (e.g., N-lauroylglycine) as a white solid.

Extraction Technique to Isolate Alkali Metal or Alkaline Metal Salt of Carboxylic Acid (e.g., Sodium N-Lauroylglycinate)

The reaction here is the same as above except THF layer is separated without acidification. The aqueous layer must be in the range of 6-10, preferably 6-8. The aqueous layer is extracted (preferably twice) with THF. Combined THF layers are concentrated on a rotary evaporator and dried in vacuo to yield the salt (e.g., N-lauroylglycinate)

Alternative Extraction Technique for the Carboxylic Acid

Besides THF extraction, carboxylic acid can be isolated by a drowning procedure and filtration. In this procedure, the reaction mixture is acidified to pH about 2-3 and added to excess of water (about 3-4 volumes compared to reaction mixture volume) with vigorous stirring using a stirring paddle. Precipitate is collected by filtration, washed with water and dried in vacuo to give carboxylic acid (e.g., N-alkanoyl-glycine).

| Reaction Monitoring of Cocoyl MonoEthylAmide (CMEA) Oxidation to Cocoyl Glycinate (CG) by HPLC | |
|---|---|
| Instrument: | Waters 2695 Separations Module equipped with a Waters 2996 Photodiode Array Detector |
| Software: | Empower Pro (version 5.00, Waters Corp.) |
| Column: | Restek Pinnacle DB C18 5 um, 4.6 × 150 mm maintained at 30° C. |
| Flow Rate: | 1 ml/min |
| Sample: | 1-2 mg/ml in 1:1 water:acetonitrile (W:ACN) containing 0.04% acetic acid (AcOH) |
| Injection Vol: | 15 uL |
| Mobile Phase: | A = 2 mM ammonium acetate, 0.04% AcOH<br>B = 2 mM ammonium acetate, 0.04% AcOH 90% aqueous ACN |
| Gradient: | 95:5 A:B to 100% B (gradient, 35 min) followed by 100% B (isocratic, 5 min) |
| Detection: | 205 nm |

Example 1

Oxidation of N-lauroylethanolamide (LMEA) in THF with 6.5 eq. of NaOCl, and Acid Work-Up 33 mg (4.5 mol %) of KBr (co-catalyst) was dissolved in 6 mL of water. Tetrahydrofuran solvent THF (31 mL), AA-TEMPO catalyst (25 mg, 2.5 mol %) and 1.5 g N-lauroylethanolamide (LMEA) were added with stirring to give a homogeneous water-white solution. Sodium hypochloride oxidizing agent (22 mL of 11.5% aq. Solution, 6.5 equivalents) and 2.3 mL of 2 NaOH (to maintain pH above 7) were mixed. The combined solution was added dropwise to the solution of LMEA and catalyst over a period of 1.5 hour. A separate aqueous layer immediately formed upon addition of the sodium hypochlorite solution. The pH of the aqueous layer was 12.7 after addition of the first 3.5 ml. The temperature was maintained below 32° C. with an ice-water bath. The reaction was stirred for 0.5 hr. more until complete conversion of LMEA to LG as determined by reversed-phase High Pressure Liquid Chromatography, abbreviated HPLC. The pH at end of the reaction was 7.6.

At completion of the reaction, the mixture was acidified to pH 3.0 (to get the purified carboxylic acid) by addition of 8.5 mL of 1 N HCl, and the layers were separated. The lower aqueous layer was extracted with 30 mL THF, and the combined THF layers were concentrated on a rotary evaporator and dried in vacuo to give N-lauroylglycine in 116% yield (residual water present).

Example 2

Oxidation of LMEA with 3.25 eq. of NaOCl, and Acid Work-Up

The procedure in Example 1 was followed, except that the amount of sodium hypochlorite was decreased to 3.25 equivalents. The isolated yield was 103% (includes residual water), showing that the oxidation works with the lower sodium hypochlorite amount.

Example 3

Oxidation of LMEA with 3.25 eq. of NaOCl, Isolation of Sodium Salt

In this example, sodium N-lauroylglycinate is obtained by a small modification of the isolation procedure. The procedure in Example 2 was followed. The pH was 7.8 upon completion of the reaction. In this case the THF layer was separated without acidification. The aq. layer was extracted twice with 30 mL of THF. After extraction, the pH of the aq. layer was 8.3. The combined THF layers were concentrated on a rotary evaporator and dried in vacuo to give sodium N-lauroylglycinate in 99% yield. Unlike N-lauroylglycine, the sodium N-lauroylglycinate dissolves in water and affords a foam upon agitation.

Example 4

Oxidation of LMEA in THF with 6.5 eq. of NaOCl, Drowning Procedure at pH=2.6

The procedure of Example 1 was followed except for the isolation step. After completion of the reaction, the mixture was acidified to pH=2.6 with 9.25 mL of 1 N HCl. The entire reaction mixture (both THF and water phases) were poured in 240 mL of water with vigorous stirring. The precipitated product was isolated by gravity filtration, and washed with 200 mL water. After air-drying, and further drying in vacuo, the product was obtained in 77% yield. The yield can be improved by better filtration techniques, e.g. by pressure filtration through a 0.45 µm or less filter.

Example 5

Oxidation of LMEA in THF with 3.25 eq. of NaOCl, Drowning Procedure, Effect of pH on Yield The procedure of Example 2 was followed except for the isolation step. After completion of the reaction, the mixture was only partially acidified (to pH=5.2 with 3.6 mL of 1 N HCl.) The entire reaction mixture (both THF and water phases) were poured in 240 mL of water with vigorous stirring. The precipitated product was isolated by gravity filtration, and washed with 240 mL water. After drying in vacuo overnight, the product was obtained in 59% yield (based on free carboxylic acid), and 55% (based on the sodium carboxylate). The lower yield than Example 4 is attributed to the larger proportion of the water-soluble sodium carboxylate at the higher pH.

Example 6

Oxidation of LMEA with 3.25 eq. of NaOCl in Water, Acid Work-Up

KBr (33 mg, 4.5 mol %) and AA-TEMPO (25 mg, 2 mol %) were dissolved in 50 mL water. 1.50 g LMEA was added and the mixture stirred 1.5 hr. to form a homogeneous suspension. Dilute sodium hypochlorite (5%) was added in 2.0 mL increments over 1.3 hr. After each addition, 0.1 N HCl was added, if necessary to maintain a pH of 8-9. Details of the addition are given in the Table below:

| 5% NaOCl (mL) | 0.1 N HCl | pH |
|---|---|---|
| 0.0 | — | 6.5 |
| 2.0 | 3.4 | 8.6 |
| 4.0 | 1.8 | 8.5 |
| 6.0 | 1.1 | 8.5 |
| 8.0 | 0.6 | 8.5 |
| 10.0 | 1.0 | 8.5 |
| 12.0 | 0.4 | 8.5 |
| 14.0 | — | 8.5 |

| 5% NaOCl (mL) | 0.1 N HCl | pH |
|---|---|---|
| 16.0 | — | 8.2 |
| 18.0 | — | 8.1 |
| 20.0 | — | 8.0 |
| 22.0 | — | 8.0 |
| 25.0 | — | 8.0 |

After stirring for 20.5 hr., the pH dropped to 5.9. The mixture was a translucent white emulsion. It was brought to pH=3.0 by addition of 3.5 mL of 1 N HCl, and extracted twice with 75 mL of THF. The combined THF layers were concentrated on a rotary evaporator and further dried in vacuo to give 1.81 g of N-lauroylglycine in 114% yield (includes residual water).

Example 7

Oxidation of N-Cocoylmonoethanolamide (CMEA) with 3.25 eq. of NaOCl using Toluene as Solvent, Acid Work-Up The oxidation reaction works on mixtures of monoethanolamides as well, including those derived from mixtures of fatty acids occurring in nature. In this example, N-cocoyl-monoethanolamine (a mixture of C-8, C-10, C-12 (major component), C-14, C-16, and C-18 monoethanolamides) was oxidized under similar conditions to give a mixture of the corresponding N-cocoylglycines. KBr (33 mg, 4.5 mol %) and AA-TEMPO (25 mg, 2 mol %) were dissolved in 6 mL of water. CMEA (1.50 g, 6.16 mmol assuming 100% LG) was dissolved 60 mL toluene at 32° C., and the solution added to the KBr and AA-TEMPO. The stirred mixture was maintained at 31-37° C. during the course of the addition and hold period. A solution of sodium hypochlorite (11 mL of 11.5% aq. solution, 3.25 eq.) and 1.15 mL of 2 N NaOH was added in 2.0 mL increments over a period of 50 min. The pH was 6.9 at the end of the addition. After 40 min. at 33° C., the pH was adjusted to 8.6 with 0.5 mL of 1 N NaOH. Stirring was continued for an additional 3.5 hr. and then the solution was allowed to cool to room temperature.

The gelatinous reaction mixture was diluted with 70 mL THF and brought to pH=2.2 with 5.5 mL of 1 N HCl. The layers were separated, and the aq. layer were extracted with an additional 20 mL THF. The combined THF layers were concentrated on a rotary evaporator and dried in vacuo to give of N-cocoylglycine in 84% yield.

Example 8

Oxidation of N-Cocoylmonoethanolamide (CMEA) with 3.25 eq. of NaOCl using Cyclohexane as Solvent, Acid Work-Up The procedure of Example 4 was followed, except that the CMEA was dissolved in 120 mL cyclohexane at 43° C. instead of toluene. After the reaction a translucent emulsion (pH=6.2) was obtained. The emulsion was brought to pH 3.1 with 3.0 mL of 1 N HCl, and extracted twice with 100 mL THF. The combined THF layers were concentrated on a rotovap and dried in vacuo to give N-cocoylglycine in 73% yield.

Comparative Example

To show that correct solvent is required, applicants conducted an experiment comparing the reaction for production of N-lauroylmonoethanolamine as set forth in Example 5 in Japanese patent application Ser. No. 10/087,554 (Assigned to Lion Corp.) to the reaction of our invention. Results are set forth below.

| Process Parameter | JP 10/087,554 | Our Invention |
| --- | --- | --- |
| Conc. of Oxidant | 5% (0.8 M) NaOCl | 11.5% (1.85 M) NaOCl |
| Amount of Oxidant | 2.8 eq. NaOCl | 3.25 eq. NaOCl |
| Solvent | Acetonitrile | THF |
| Phases | Acetonitrile was dissolved in water and only one liquid phase formed | 2-Phase System: Separate THF and aqueous layers. Two liquid phases were present |
| Location of LMEA | LMEA undissolved in CH$_3$CN/water - thick slurry was obtained. | LMEA dissolved in THF layer. |
| Added base | No NaOH added to NaOCl | 2 N NaOH added to NaOCl |
| pH Range | pH 5.5-6.6 during reaction | pH 13.2-7.4 during reaction |
| Reaction Temperature | 33-35° C. | 24-26° C. |
| Reaction Time | 6 hr. including NaOCl addition time | 2 hr. including NaOCl addition time. |
| Isolated Yield | 81% | >100% (water present) |
| Purity (HPLC Area %) | 30.6% | 68.5% |

Summary of Oxidation Examples

A summary of the Examples for oxidation of LMEA to LG is set forth in the Table below.

| Ex. No | NaOCl:Substrate | NaOCl Conc. | Solvent | Reac Time (hr.) | Initial Temp (° C.) | Peak Temp (° C.) | Initial pH | Final pH | Isolation Method | Work-up pH | Yield as Acid | Yield as Salt |
| --- | --- | --- | --- | --- | --- | --- | --- | --- | --- | --- | --- | --- |
| 1 | 6.5:1 | 11.5% | THF | 2 | 24 | 32 | 12.71 | 7.57 | THF Extraction | 3.0 | 116% | 107% |
| 2 | 3.25:1 | 11.5% | THF | 2 | 24 | 26 | 9.89 | 7.61 | THF Extraction | 2.1 | 103% | 95% |
| 3 | 3.25:1 | 11.5% | THF | 2 | 25.4 | 26.9 | 10.3 | 7.8 | THF Extraction | 8.3 | 108% | 99% |
| 4 | 6.5:1 | 11.5% | THF | 2 | 24.8 | 30.2 | 11.56 | 7.24 | Water Drowning | 2.6 | 77% | 71% |
| 5 | 3.25:1 | 11.5% | THF | 3 | 23 | 25.2 | 10.35 | — | Water Drowning | 5.2 | 59% | 55% |
| 6 | 3.25 | 5% | Water | 21[a] | 19.5 | 19.5 | 8.56 | 7.81 | THF Extraction | 2.5 | 114% | 105% |

[a] Actual reaction time may be less.

A summary of the Examples of the oxidation of N-cocoylmethanolamide to N-cocoylglycine is set forth in the Table below.

| Ex. No | NaOCl:Substrate | NaOCl Conc. | Solvent | Reac Time (hr.) | Initial Temp (° C.) | Peak Temp (° C.) | Initial pH | Final pH | Isolation Method | Work-up pH | Yield as Acid[b] | Yield as Salt[b] |
| --- | --- | --- | --- | --- | --- | --- | --- | --- | --- | --- | --- | --- |
| 7 | 3.25:1 | 11.5% | Toluene | 6[a] | 31 | 38 | — | 8.9 | THF Extraction | 2.2 | 84% | 78% |
| 8 | 3.25:1 | 11.5% | Cyclohexane | 16[a] | 38.5 | 41 | — | 6.2 | THF Extraction | 3.1 | 73% | 67% |

[a] Actual reaction time may be less.
[b] Assume CMEA and CG are each the corresponding 100% C-12 compounds.

The invention claimed is:

1. A process for converting an alcohol comprising amide group to corresponding carboxylic acid in yield ≧75% which process comprises reacting:

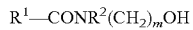

wherein $R^1$ is linear or branched alkyl or alkenyl group having 7 to 22 carbon atoms; $R^2$ is H, an alkyl or hydroxyalkyl group with 1 to 6 carbon atom(s); and m is an integer from 1 to 6, with an oxidizing agent in the presence of a hindered nitroxide radical and optional co-catalyst, wherein the solvent in which the reaction takes place is selected such that, in the presence of the oxidizing agent, the solvent layer separates from the aqueous layer, and the amidoalcohol partitions into the organic liquid solvent layer to thereby permit the high yields noted;

wherein said solvent is tetrahydrofuran.

2. A process according to claim 1, wherein the alcohol comprising amide group is an alkanoylmonoalkanolamine.

3. A process according to claim 2, wherein the alkanoylmonoalkanolamine is lauroyl monoalkanolamide or cocomonoethanolamide.

4. A process according to claim 1, wherein the oxidizing agent is selected from the group consisting of chlorine, a hypochlorite, chloroisocyanuric acid, and mixtures thereof.

5. A process according to claim 1 wherein the oxidizing agent is selected from the group consisting of NaOBr, bromosuccinimide, bromoisocyanuric acid, peracids, oxone, $H_2O_2$ and mixture thereof.

6. A process according to claim 1, wherein oxidizing agent is present in amount from equimolar to 8 molar.

7. A process according to claim 1, wherein the nitroxide catalyst is 4-acetamido-TEMPO.

8. A process according to claim 1, where, in addition to hindered nitroxide radical co-catalyst is used.

9. A process according to claim 8, wherein co-catalyst is alkali metal halide or alkali earth metal halide.

10. A process according to claim 1, wherein solvents contain substantially no anti-oxidants.

11. A process according to claim 1 where base is additionally added to the reaction.

12. A process according to claim 1 wherein sufficient base is added to maintain pH above 6.

* * * * *